United States Patent
Sanders et al.

(10) Patent No.: US 12,295,700 B2
(45) Date of Patent: May 13, 2025

(54) SYSTEMS AND METHODS FOR ESTIMATION OF BLOOD FLOW CHARACTERISTICS USING REDUCED ORDER MODEL AND/OR MACHINE LEARNING

(71) Applicant: HeartFlow, Inc., Mountain View, CA (US)

(72) Inventors: Travis Michael Sanders, Plano, TX (US); Sethuraman Sankaran, Palo Alto, CA (US); Leo Grady, Darien, CT (US); David Spain, Portland, OR (US); Nan Xiao, San Jose, CA (US); Jin Kim, Daly City, CA (US); Charles A. Taylor, Atherton, CA (US)

(73) Assignee: Heartflow, Inc., Mountain View, CA (US)

( * ) Notice: Subject to any disclaimer, the term of this patent is extended or adjusted under 35 U.S.C. 154(b) by 0 days.

(21) Appl. No.: 18/661,943

(22) Filed: May 13, 2024

(65) Prior Publication Data
US 2024/0298894 A1    Sep. 12, 2024

Related U.S. Application Data

(63) Continuation of application No. 18/302,291, filed on Apr. 18, 2023, now Pat. No. 12,004,841, which is a (Continued)

(51) Int. Cl.
*G16H 30/40* (2018.01)
*A61B 5/00* (2006.01)
(Continued)

(52) U.S. Cl.
CPC ........ *A61B 5/0044* (2013.01); *A61B 5/02007* (2013.01); *G16B 40/20* (2019.02);
(Continued)

(58) Field of Classification Search
CPC ... A61B 5/0044; A61B 5/02007; A61B 5/026; A61B 5/7275; G16B 40/20; G16B 45/00;
(Continued)

(56) References Cited

U.S. PATENT DOCUMENTS 8,315,812 B2   11/2012  Taylor
9,087,147 B1 *  7/2015  Fonte ................... A61B 5/0263
(Continued)

FOREIGN PATENT DOCUMENTS

CN    104854592 A    8/2015
CN    103270513 B    6/2017
(Continued)

OTHER PUBLICATIONS

Office Action issued in Chinese Patent Application No. 201780071286.4 on Sep. 21, 2022.

*Primary Examiner* — Stephen P Coleman
(74) *Attorney, Agent, or Firm* — Bookoff McAndrews, PLLC

(57) ABSTRACT

Systems and methods are disclosed for determining blood flow characteristics of a patient. One method includes: receiving, in an electronic storage medium, patient-specific image data of at least a portion of vasculature of the patient having geometric features at one or more points; generating a patient-specific reduced order model from the received image data, the patient-specific reduced order model comprising estimates of impedance values and a simplification of the geometric features at the one or more points of the vasculature of the patient; creating a feature vector comprising the estimates of impedance values and geometric features for each of the one or more points of the patient-specific reduced order model; and determining blood flow characteristics at the one or more points of the patient-specific reduced order model using a machine learning
(Continued)

algorithm trained to predict blood flow characteristics based on the created feature vectors at the one or more points.

20 Claims, 6 Drawing Sheets

Related U.S. Application Data continuation of application No. 17/169,912, filed on Feb. 8, 2021, now Pat. No. 11,653,833, which is a continuation of application No. 15/709,195, filed on Sep. 19, 2017, now Pat. No. 10,945,606.

(60) Provisional application No. 62/396,965, filed on Sep. 20, 2016.

(51) Int. Cl.
| | |
|---|---|
| *A61B 5/02* | (2006.01) |
| *G16B 40/20* | (2019.01) |
| *G16H 50/20* | (2018.01) |
| *G16H 50/50* | (2018.01) |
| *G16H 50/70* | (2018.01) |
| *A61B 5/026* | (2006.01) |
| *G16B 45/00* | (2019.01) |

(52) U.S. Cl.
CPC .............. *G16H 30/40* (2018.01); *G16H 50/20* (2018.01); *G16H 50/50* (2018.01); *G16H 50/70* (2018.01); *A61B 5/026* (2013.01); *G16B 45/00* (2019.02)

(58) Field of Classification Search
CPC ........ G16B 99/00; G16H 30/40; G16H 50/20; G16H 50/50; G16H 50/70
USPC ........................................................ 600/481
See application file for complete search history.

(56) References Cited

U.S. PATENT DOCUMENTS

| | | | |
|---|---|---|---|
| 9,424,395 | B2 | 8/2016 | Sankaran et al. |
| 2014/0336995 | A1 | 11/2014 | Singer |
| 2015/0272448 | A1 | 10/2015 | Fonte et al. |
| 2016/0180055 | A1 | 6/2016 | Fonte et al. |
| 2016/0196384 | A1 | 7/2016 | Mansi et al. |

FOREIGN PATENT DOCUMENTS

| | | |
|---|---|---|
| JP | 2012024582 A | 2/2012 |
| JP | 2013534154 A | 9/2013 |
| JP | 2014534889 A | 12/2014 |
| JP | 2016500548 A | 1/2016 |
| JP | 2016511682 A | 4/2016 |
| WO | 2016001017 A1 | 1/2016 |

\* cited by examiner

SYSTEMS AND METHODS FOR ESTIMATION OF BLOOD FLOW CHARACTERISTICS USING REDUCED ORDER MODEL AND/OR MACHINE LEARNING

RELATED APPLICATION(S)

This application is a continuation of and claims the benefit of priority to U.S. application Ser. No. 18/302,291, filed Apr. 18, 2023, which in turn is a continuation of and claims the benefit of priority to U.S. application Ser. No. 17/169,912, filed Feb. 8, 2021, now U.S. Pat. No. 11,653,833, which in turn is a continuation of and claims the benefit of priority to U.S. application Ser. No. 15/709,195, filed Sep. 19, 2017, now U.S. Pat. No. 10,945,606, which claims priority to U.S. Provisional Application No. 62/396,965, filed Sep. 20, 2016, each of which is incorporated herein by reference in its entirety.

FIELD OF THE DISCLOSURE

Various embodiments of the present disclosure relate generally to diagnostics and treatment planning of vascular system(s). More specifically, particular embodiments of the present disclosure relate to systems and methods for estimation of blood flow characteristics using reduced order models and/or machine learning.

BACKGROUND

Blood flow in the coronary arteries may provide useful information, including the presence or extent of ischemia, blood perfusion to the myocardium, etc. Since direct measurement of blood flow in small arteries may be difficult, blood flow can be simulated by solving the Navier-Stokes equations on a patient-specific, 3-dimensional (3D) geometry derived from medical imaging data including cardiac computerized tomography (CT) scans, magnetic resonance imaging (MRI), ultrasound, etc. To expedite the solution process, the 3D geometry can be simplified to a one dimensional skeleton of centerlines parameterized by area or radii, and blood flow characteristics (e.g., pressures, flow rate, etc.) may be calculated along these centerlines, for example, by solving a simplification of the Navier-Stokes equations. These techniques may enable a significantly faster computation of the solution to Navier-Stokes equations, but they may not be as accurate as solving the Navier-Stokes equations for a 3D geometry. There is a desire for methods that may provide a more precise and accurate calculation of blood flow characteristics in localized regions of an anatomical model, where a method involving the simplification to a 1D geometry is not accurate enough. Such a desired method may retain accuracy while significantly improving computational time. There is also a desire for a method that utilizes these models to determine the optimal geometric parameterization that would yield an optimal solution and/or improve the knowledge of geometrical characteristics of a patient's anatomy, and thereby enhance medical imaging.

SUMMARY

Described below are various embodiments of the present disclosure of systems and methods for the estimation of blood flow characteristics using reduced order models and/or machine learning.

One method includes: receiving, in an electronic storage medium, patient-specific image data of at least a portion of vasculature of the patient having geometric features at one or more points; generating a patient-specific reduced order model from the received image data, the patient-specific reduced order model comprising estimates of impedance values and a simplification of the geometric features at the one or more points of the vasculature of the patient; creating a feature vector comprising the estimates of impedance values and geometric features for each of the one or more points of the patient-specific reduced order model; and determining blood flow characteristics at the one or more points of the patient-specific reduced order model using a machine learning algorithm trained to predict blood flow characteristics based on the created feature vectors at the one or more points.

In accordance with another embodiment, a system for estimation of blood flow characteristics using reduced order models and/or machine learning comprises: a data storage device storing instructions for estimation of blood flow characteristics using reduced order models and/or machine learning; and a processor configured for: receiving, in an electronic storage medium, patient-specific image data of at least a portion of vasculature of the patient having geometric features at one or more points; generating a patient-specific reduced order model from the received image data, the patient-specific reduced order model comprising estimates of impedance values and a simplification of the geometric features at the one or more points of the vasculature of the patient; creating a feature vector comprising the estimates of impedance values and geometric features for each of the one or more points of the patient-specific reduced order model; and determining blood flow characteristics at the one or more points of the patient-specific reduced order model using a machine learning algorithm trained to predict blood flow characteristics based on the created feature vectors at the one or more points.

In accordance with another embodiment, a non-transitory computer readable medium for use on a computer system containing computer-executable programming instructions for estimation of blood flow characteristics using reduced order models and/or machine learning, the method comprising: receiving, in an electronic storage medium, patient-specific image data of at least a portion of vasculature of the patient having geometric features at one or more points; generating a patient-specific reduced order model from the received image data, the patient-specific reduced order model comprising estimates of impedance values and a simplification of the geometric features at the one or more points of the vasculature of the patient; creating a feature vector comprising the estimates of impedance values and geometric features for each of the one or more points of the patient-specific reduced order model; and determining blood flow characteristics at the one or more points of the patient-specific reduced order model using a machine learning algorithm trained to predict blood flow characteristics based on the created feature vectors at the one or more points.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

The steps described in the methods may be performed in any order, or in conjunction with any other step. It is also contemplated that one or more of the steps may be omitted for performing the methods described in the present disclosure.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Various embodiments of the present disclosure may provide systems and methods for estimation of blood flow characteristics using reduced order models and/or machine learning. For purposes of this disclosure, blood flow characteristics may include, but are not limited to, blood pressure, fractional flow reserve (FFR), blood flow rate or flow velocity, a velocity or pressure field, hemodynamic forces, and organ and/or tissue perfusion characteristics. At least some embodiments of the present disclosure may provide the benefits of delivering a faster computation of blood flow characteristics from image data, e.g., through the use of a reduced order model, but ensuring a more accurate computation of the blood flow characteristics, e.g., by utilizing a trained machine learning algorithm. It is contemplated that to achieve these benefits, other models with simplified geometry other than a reduced order model may also be used in lieu of or in addition to the reduced order model.

Figure 1:
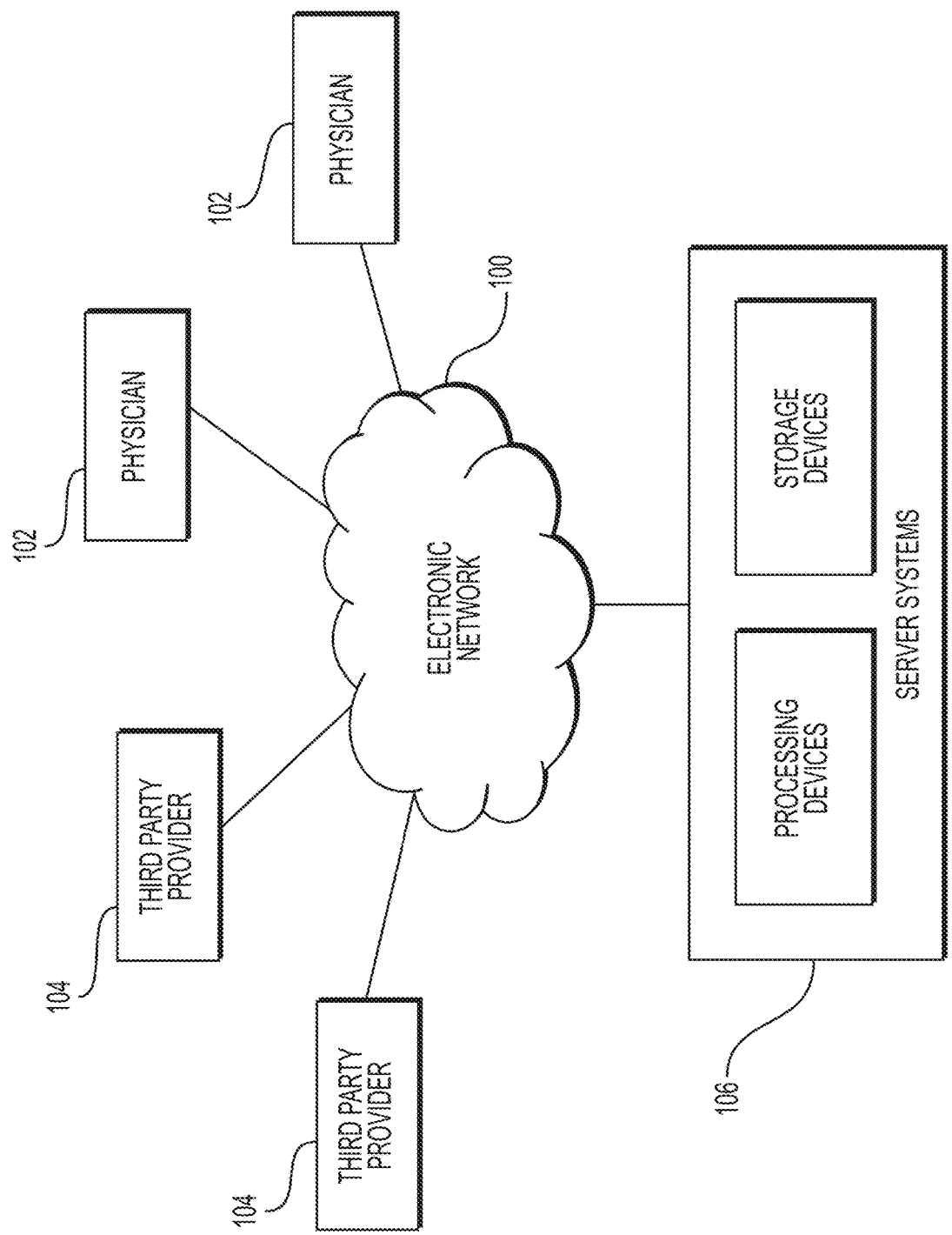
FIG. 1 is a block diagram of an exemplary system and network 100 for predicting or estimating blood flow characteristics using reduced order models and/or machine learning, according to an exemplary embodiment of the present disclosure.

Referring now to the figures, FIG. 1 depicts a block diagram of an exemplary system 100 and network for estimation of blood flow characteristics using reduced order models and/or machine learning, according to an exemplary embodiment. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific and/or reference anatomical images, physiological measurements, and/or information, including, but not limited to, geometrical and/or anatomical characteristics of the vessels of interest of a patient, blood flow characteristics, impedance values for vessels of interest, etc. In some embodiments, physicians 102 and/or third party providers 104 may also obtain reference values pertaining to blood flow characteristics, as it relates to a reduced order or lumped parameters model. For example, for a reduced order model simplifying blood flow characteristics to a one dimensional electrical circuit, physicians 102 and/or third party providers 104 may obtain resistance, capacitance, and/or inductance values from a library of parameters or a look-up table based on the blood flow characteristics that may be simplified.

Physicians 102 and/or third party providers 104 may transmit the anatomical images, physiological information, and/or information on vessels of interest to server systems 106 over the electronic network 100. Server systems 106 may include storage devices for storing images and data received from physicians 102 and/or third party providers 104. Server systems 106 may also include processing devices for processing images and data stored in the storage devices.

Figure 2:
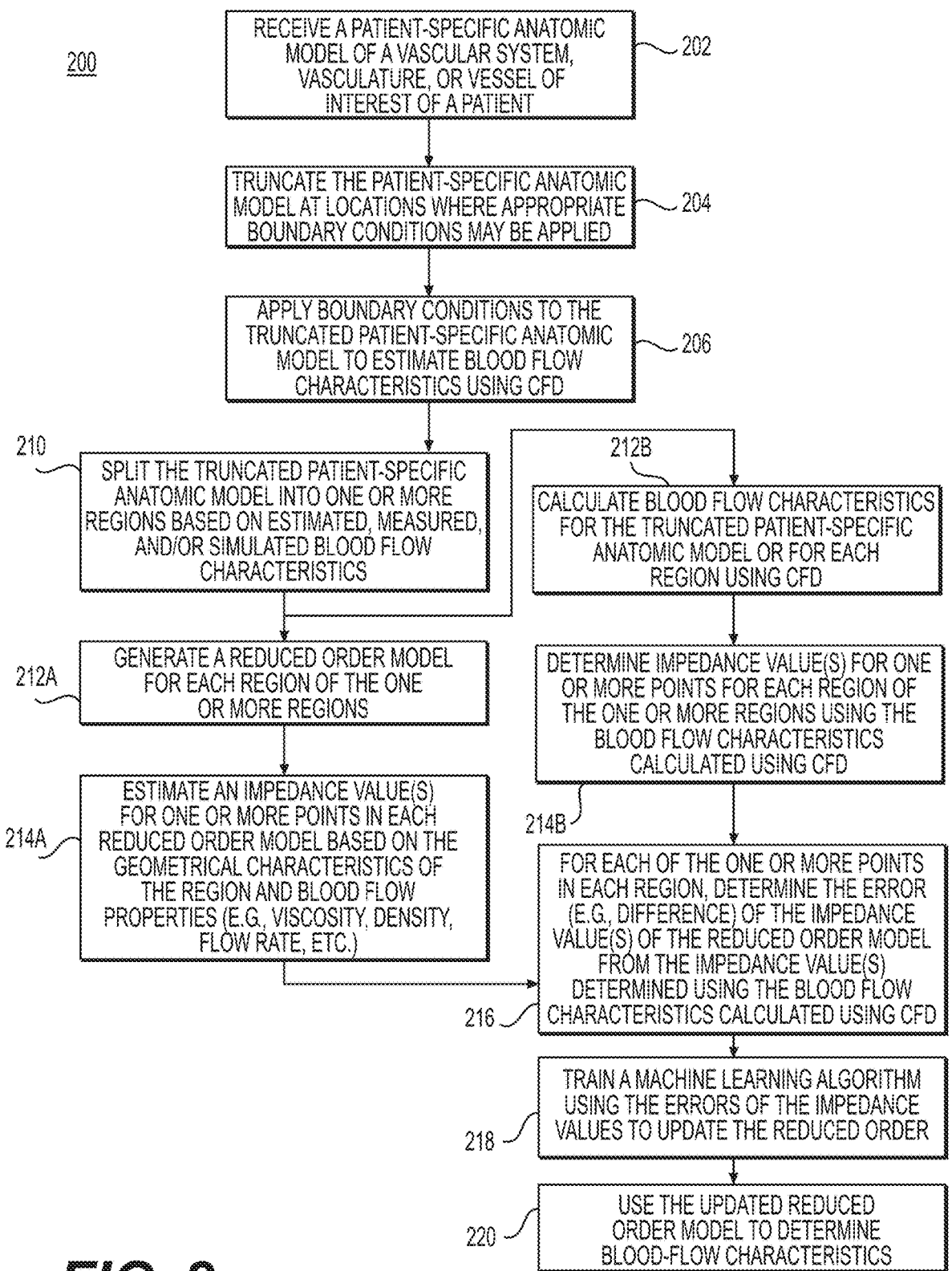
FIG. 2 is a block diagram of a general method 200 of predicting or estimating blood flow characteristics using reduced order models and/or machine learning, according to an exemplary embodiment of the present disclosure.

FIG. 2 depicts a method 200 of estimating blood flow characteristics using reduced order models and/or machine learning, according to an exemplary embodiment of the present disclosure.

In some embodiments, step 202 of method 200 may include receiving a patient-specific anatomic model of a vascular system, vasculature, or a vessel of interest of a patient. In some embodiments, instead of a model, patient-specific image data may be received of a vascular system, vasculature, or a vessel of interest of a patient. The vascular system, under which a vessel of interest or a vasculature may belong, may include, a coronary vascular model, a cerebral vascular model, a peripheral vascular model, a hepatic vascular model, a renal vascular model, a visceral vascular model, or any vascular model with vessels supplying blood that may be prone to stenotic lesions or plaque formation. In some embodiments, other patient data of the vascular system, vasculature, or the vessel of interest of the patient may be received, for example, measured blood flow characteristics and/or properties. The image data and/or blood flow characteristics and/or properties may be non-invasively and/or invasively acquired from a patient (e.g., via a scanning modality or medical device), or may be acquired via population studies (e.g., based on similarities with the patient).

Step 204 may include truncating the patient-specific anatomic model at locations where appropriate boundary conditions may be applied. This truncation may be performed such that regions of vessel narrowing can be captured, e.g., distal to the locations of disease in the arteries visible in the imaging modality, and encompassing one or more blood vessels identified from anatomic information (e.g., anatomic information received in step 202).

Step 206 may include applying boundary conditions to the truncated patient-specific anatomic model to estimate blood flow characteristics. The estimated blood flow characteristics may provide the approximation that may be used to generate a reduced order model (e.g., as in 212A). In some embodiments, the applied boundary conditions may be used to eventually solve for blood flow characteristics using computational fluid dynamics (CFD) (e.g., 212B). The boundary conditions provide information about the hemodynamics at the boundaries of the three dimensional model, e.g., the inflow boundaries or inlets, the outflow boundaries or outlets, the vessel wall boundaries, etc. The inflow boundaries or inlets may include the boundaries through which flow is directed into the anatomy of the three-dimensional model, such as at the aorta. The inflow boundary may be assigned, e.g., with a prescribed value or field for velocity, flow rate, pressure, or other characteristic, for example, by coupling a heart model and/or a lumped parameter model to the boundary, etc. The flow rate at the aorta may be estimated by cardiac output, measured directly or derived from the patient's mass using scaling laws. In some embodiments, flow rate of the aorta may be estimated by cardiac output using methods described in U.S. Pat. No. 9,424,395, ("Method and system for sensitivity analysis in modeling blood flow characteristics") filed Apr. 17, 2013, and hereby incorporated by reference in entirety herein.

For example, net cardiac output (Q) may be calculated from body surface area (BSA) as $$Q = \frac{1}{60} BSA^{1.15}$$

(cardiac output). The body surface area (BSA) may be calculated from height (h) and weight (w) as:

$$BSA = \sqrt{\frac{hw}{3600}}.$$

Coronary Flow rate ($q_{cor}$) may be calculated from myocardial mass ($m_{myo}$) as:

$$q_{cor} = c_{dil} \frac{5.09}{60} m_{myo}^{0.75},$$

where $C_{dil}$ is a dilation factor. Thus, the flow in the aorta can be Q–$q_{cor}$.

Likewise, alternatively or additionally, step 210 may include determining blood flow characteristics for the truncated patient-specific anatomic model using CFD.

Thus, step 210 may include splitting the truncated patient-specific anatomic model into one or more regions. The splitting may be performed based on an estimation of blood flow characteristics from the applied boundary conditions (e.g., from step 206). Alternatively or additionally, step 210 may include splitting the truncated patient-specific anatomic model into one or more regions based on the blood flow characteristics that were determined using CFD (e.g., from step 212B described herein). In some embodiments, measurements of blood flow characteristics for at least a part of the vascular system, vasculature, or vessel of interest of the patient may also be received along with a patient-specific anatomic model of the vascular system, vasculature, or vessel of interest (e.g., as in step 202). In such embodiments, the truncated patient-specific anatomic model may be split into one or more regions based on the measured blood flow characteristics. The model may be split into different regions based on flow characteristics, e.g., (i) ostial bifurcation, (ii) non-ostial bifurcation, (iii) stenosis, (iv) area expansion post-stenosis, (v) healthy, etc. Each of these regions may be further split into sub-regions with a pre-determined length.

In some embodiments, step 204 and 210 may be combined (e.g., truncating at regional boundaries), or one of the two steps may be skipped (e.g., using just a single region for the method).

Step 212A may include generating a reduced order model for each region of the one or more regions. The reduced order model may parameterize the geometry using a set of radii along centerlines and may solve simplified Navier-Stokes equations by making an assumption on the blood flow profile. Since a reduced order or lumped parameter model characteristically may not have geometric features of a more complicated (e.g., 3D) model, the reduced order or lumped parameter model may depict a simplification of the geometric features ("simplified geometric features") of the more complicated model, e.g., the geometric features be described in terms of a singular dimension. For example, a three-dimensional geometric feature of a narrowing of a circumference of a vessel may be a simplified geometric feature of a reduction in vessel diameter on a reduced order and/or lumped parameter model. Thus, 3D geometric may be represented by a set of radii along a centerline for a reduced order and/or lumped parameter model. It is contemplated, however, that geometric features, e.g., from the original 3D anatomy or model, may be quantified and/or discretized, for example, for purposes of creating feature vectors in a machine learning algorithm. Examples of geometric features may include, but are not limited to, distance from the nearest bifurcation, distance from the ostium, minimum upstream diameter, etc.

Step 214A may include estimating an impedance value for one or more points in each reduced order model (or one or more of the reduced order models from step 212). The impedance values may involve an estimation of blood flow characteristics based on a preliminary reduced order and/or lumped parameter model. For example, the blood flow characteristics may be estimated from boundary conditions or measured from the patient. In some embodiments, these reduced order models may be based on the geometrical characteristics of the region. In one embodiment, these reduced order models may be further based on blood flow properties (e.g., viscosity, density, flow rate, etc.) and/or blood flow characteristics. In such embodiments, measurements of blood flow properties for at least a part of the vascular system, vasculature, or vessel of interest of the patient may also be received along with a patient-specific anatomic model of the vascular system, vasculature, or vessel of interest (e.g., as in step 202). Likewise, physiological and/or phenotypic parameters of the patient may also affect the estimation of the impedance values, and these parameters may also be received (e.g., in step 202). In some embodiments, a reduced order and/or lumped parameter model may simplify an anatomical model to a one-dimensional electric circuit representing the pathway of blood flow through the anatomic model. In such embodiments, the impedance may be represented by resistance values (and other electrical features) on the electric circuit.

While steps 212A and 214A, described above, may describe a method for estimating and/or determining the impedance values via a reduced order and/or lumped parameter model, steps 212B and 214B may describe a method for estimating and/or determining impedance values via a CFD analysis.

For example, step 212B may include solving for blood flow characteristics for using a CFD analysis or simulation. Step 212B may utilize the applied boundary conditions (e.g., from 206) in the CFD analysis or simulation.

Furthermore step 212B may include calculating blood flow characteristics for the entire system (e.g., represented by the patient-specific anatomic model of the vascular system, vasculature, or vessel of interest of the patient), the truncated patient-specific anatomic model, or for each region of the one or more regions (split in step 210) of the patient-specific anatomic model. For example, step 212B may include using the boundary conditions applied in step 206 to solve the equations governing blood flow for velocity and pressure. In one embodiment, step 212B may include the computing of a blood flow velocity field or flow rate field for one or more points or areas of the anatomic model, using the assigned boundary conditions. This velocity field or flow rate field may be the same field as computed by solving the equations of blood flow using the physiological and/or boundary conditions provided above. Step 212B may further include solving scalar advection-diffusion equations governing blood flow at one or more locations of the patient-specific anatomic model.

Step 214B may include determining an impedance value for one or more points for each region of the one or more regions using the blood flow characteristics calculated using CFD. In some embodiments, the impedance value may be an approximation and/or simplification from a blood flow characteristic solved using CFD (as opposed to an estimation from a reduced order and/or lumped parameter model in step 212A).

For steps 214A and/or 214B, the impedance values may include, for example, a resistance value, a capacitance value, and/or inductance value.

The resistance may be constant, linear, or non-linear, e.g., depending on the estimated flow rate through a corresponding segment of a vessel. For more complex geometries, such as a stenosis, the resistance may vary with flow rate. Resistances for various geometries may be determined based on a computational analysis (e.g., a finite difference, finite volume, spectral, lattice Boltzmann, particle-based, level set, isogeometric, or finite element method, or other computational fluid dynamics (CFD) analytical technique), and multiple solutions from the computational analysis performed under different flow and pressure conditions may be used to derive patient-specific, vessel-specific, and/or lesion-specific resistances. The results may be used to determine resistances for various types of features and geometries of any segment that may be modeled. As a result, deriving patient-specific, vessel-specific, and/or lesion-specific resistances as described above may allow the computer system to recognize and evaluate more complex geometry such as asymmetric stenosis, multiple lesions, lesions at bifurcations and branches and tortuous vessels, etc.

Capacitors may be also included as an impedance and/or as a feature in the reduced order or lumped parameter models. Capacitance may be determined, e.g., based on elasticity of the vessel walls of the corresponding segment. Inductors may be included, and inductance may be determined, e.g., based on inertial effects related to acceleration or deceleration of the blood volume flowing through the corresponding segment.

The individual values for resistance, capacitance, inductance, and other variables associated with other electrical components used in the reduced order and/or lumped parameter models may be derived based on data from many patients, and similar vessel geometries may have similar values. Thus, empirical models may be developed from a large population of patient-specific data, creating a library of values corresponding to specific geometric features that may be applied to similar patients in future analyses. Geometries may be matched between two different vessel segments to automatically select the values for a segment or vessel of interest of a patient from a previous simulation.

Step 216 may include, for the one or more points in each region, determining the error (e.g., difference) of the impedance value of the reduced order model from the impedance value determined using the blood flow characteristics calculated using CFD. Step 218 may include training a machine-learning algorithm using the errors of the impedance values to update the reduced order model with an appropriate set of features. A machine learning regressor may be trained on the errors calculated in step 216. Therefore, after solving the reduced order model and calculating errors with respect to the blood flow characteristics calculated using CFD, step 218 may include defining a set of features (e.g., geometric, clinical, flow-related, etc.), and mapping the features to the errors to estimate a better blood flow solution. A set of features encompassing geometric features (e.g. degree of stenosis, distance from ostium, distance from bifurcation, worst upstream stenosis etc.), flow-related features (e.g. downstream boundary conditions), and/or features directly calculated from the reduced order model (e.g. resistances) may be used. Different candidate machine-learning algorithms or regressors may be utilized (e.g., random decision forests, neural networks, multi-layer perceptrons, etc.). The trained machine learning algorithm may be used to update the reduced order model(s), e.g., by determining new (or corrected) impedance values. Step 220 may include using the updated reduced order model to determine blood flow characteristics. For example, the learned impedances may be used to estimate the flow and pressure. Method 400A of FIG. 4A may describe the training of such a machine learning algorithm in further detail.

Alternatively, the regressor may be trained to predict an idealized geometry to match the CFD or measured values. This idealized geometry determined using a machine learning algorithm, may be used as the inputs to this system (e.g., optimizing the simplified geometric features of the reduced order and/or lumped parameter models) or as a part of a system enabling fast computation of the Navier-Stokes equations. For example, the regressor may be used to determine the optimal parameterization and/or simplification of geometric features for a reduced order model, so that the reduced order model may more accurately compute blood flow characteristics. Method 400B or FIG. 4B may describe the training of such a machine learning algorithm in further detail.

In some embodiments, the results of method 200 may be output to an electronic storage medium or display. The results may include blood flow characteristics. The results may be visualized using color maps.

Figure 3:
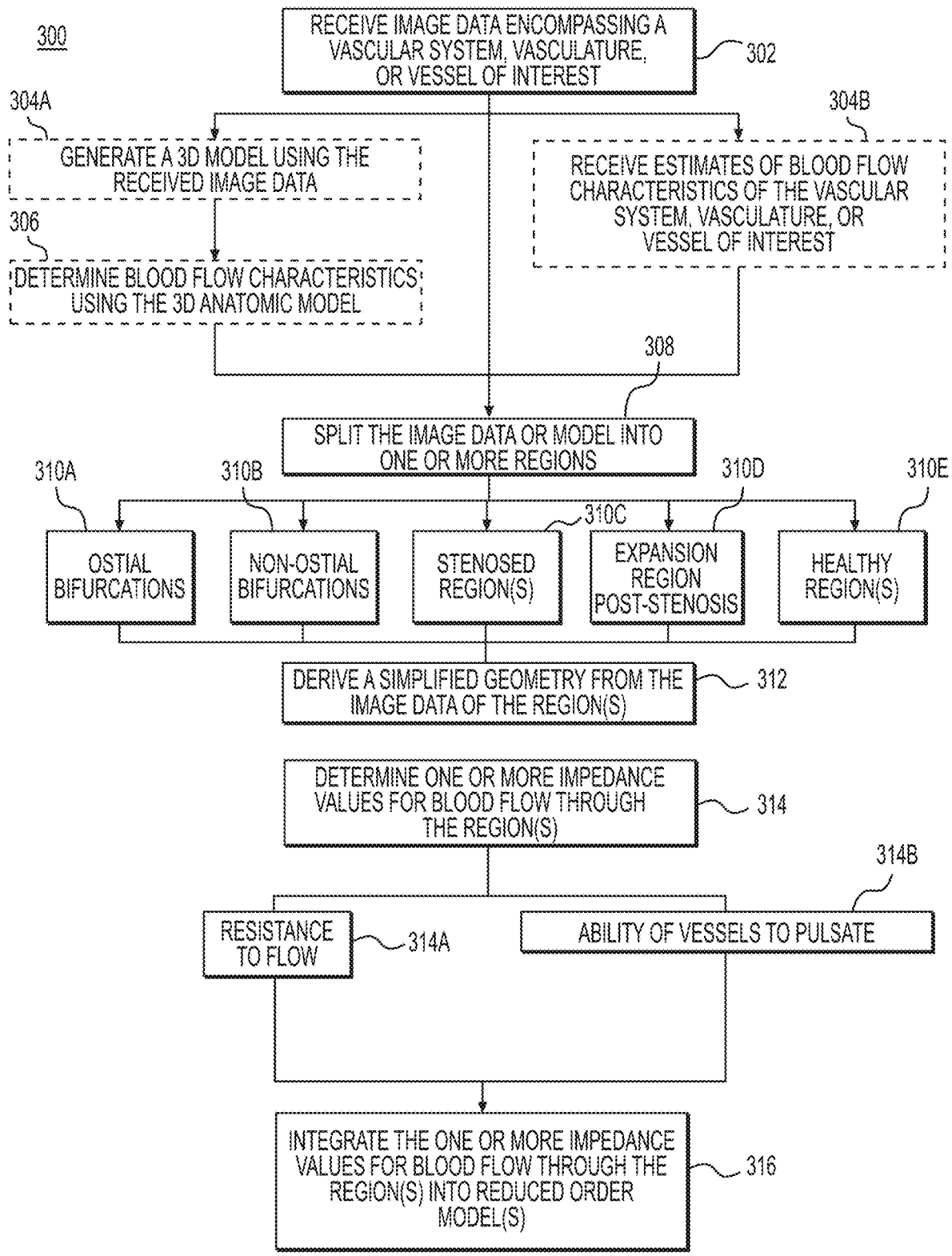
FIG. 3 is a block diagram of a general method 300 of generating a reduced order model from image data and using the reduced order model to determine impedance values, according to an exemplary embodiment of the present disclosure.

FIG. 3 is a block diagram of a general method 300 of generating a reduced order model from image data and using the reduced order model to determine impedance values, according to an exemplary embodiment of the present disclosure.

Step 302 of method 300 may include receiving image data (or anatomic images and/or information) encompassing vessels or a vascular region of interest. In such embodiments, the image data, anatomic images, and/or information may be stored in an electronic storage medium. The vessels of interest may include, for example, various vessels of the coronary vascular system. In other embodiments, the vessels of other vascular systems may also be captured, including, but not limited to, coronary vascular system, a cerebral vascular system, a peripheral vascular system, a hepatic vascular system, a renal vascular system, a visceral vascular system, or any vascular system with vessels supplying blood that may be prone to stenotic lesions or plaque formation. The anatomical images and/or information may be extracted from images and/or image data generated from a scanning modality (e.g., forms of magnetic resonance (MR), forms of computed tomography (CT), forms of positron emission tomography (PET), X-Ray, etc.) and/or may be received from an electronic storage device (e.g. hard drive).

Step 308 may include splitting the model into one or more regions. In some embodiments, the splitting may be based on anatomical and/or estimates of blood flow characteristics. For example, these anatomical and/or blood flow characteristics may include, but are not limited to, ostial bifurcations 310A, non-ostial bifurcations 310B, stenosed region(s) 310C, expansion regions (e.g., post-stenosis) 310D, and healthy region(s) 310E. Other region splitting schemes based on different region data characteristics could also be pursued. In some embodiments, estimates of blood flow characteristics may be obtained via steps 304A and 306, and/or 304B.

For example, step 304A may include generating a three-dimensional (3D) anatomical model encompassing the vessels of interest using the received image data. In other embodiments, a 2D anatomical model may be generated, or an anatomical model with a temporal dimension may be generated. The anatomical model may be generated from received or stored anatomic images and/or information encompassing the vessels of interest of a patient (e.g., from step 302). In such embodiments, the construction of a 3D anatomical model may involve segmentation or related methods. Segmentation may occur by placing seeds, e.g., based on an extracted centerline, and using the intensity values from the image data to form one or more segmentation models (e.g., "threshold-based segmentation," as described in U.S. Pat. No. 8,315,812, filed Jan. 25, 2011, which is hereby incorporated herein in its entirety). Segmentation may also occur by locating the edges (e.g., of a lumen) using the intensity values of the image data, placing seeds, and expanding the seeds, until an edge has been reached (e.g., "threshold-based segmentation", as described in U.S. Pat. No. 8,315,812, filed Jan. 25, 2011, which is hereby incorporated herein in its entirety). In some embodiments, the marching cube algorithm may also be used for segmentation.

Step 306 may include determining blood flow characteristics of the vessels of interest using the 3D anatomical model.

Additionally or alternately, the splitting in step 308 may occur from received estimates of blood flow characteristics. For example, step 304B may include receiving estimates of blood flow characteristics of the vessels of interest, e.g., from population derived data, patient studies, or measurements. Step 312 may include deriving a simplified geometry from the split image data of the region(s). In one embodiment, the geometry may be derived from the original 3-D geometry of the image data received in step 302 or from the 3-D model generated in step 304A. The geometry may be defined by centerline points and an associated radius. In one embodiment, an optimal 1-D geometry may be derived or learned that results in the optimal performance of 1-D blood flow simulation compared to the 3-D blood flow simulations.

Once the geometry is defined, impedance values at each centerline point $x_i$ can be computed based on the defined geometry. Thus, step 314 may include determining one or more impedance values for blood flow through the region(s). The impedances may include, for example, blood flow characteristics (e.g., pressure, flow rate, etc.) or their analogous representations or simplifications (e.g., resistance, capacitance, inductance, etc.) Thus, step 314 may include determining one or more impedance values for blood flow through the region(s). For example, a fluid-mechanic impedance may be estimated from data. In some cases, such data may be estimated from 3D blood flow simulations (e.g., as in step 306 or steps 210B, 212B, and 214B of FIG. 2), or the data may be from/derived from measurements of flow and pressure (e.g., as in step 304B). Impedance may include resistance to flow (ratio of blood pressure to flowrate) 314A, ability of the coronary arteries to pulsate (from the elastance of the artery) 314B, etc.

The pressure at each centerline point $x_i$ may be computed starting with the given aortic pressure by, $P_{i+1} - P_i = (R_{poisseuille} + R_{bernoulli} + R_{loss})Q_i$, where $$R_{poisseuille} = -\frac{8\mu L}{\pi r_i^4};$$

$$R_{bernoulli} = \frac{\rho L \frac{dA}{dx}}{A_i^3} Q_i;$$

μ=blood viscosity;

$$L = \|x_{i+1} - x_i\|;$$

$r_i$=radius at point $x_i$;
ρ=blood density;
$A_i$=cross-sectional area (area of circle with radius $r_i$); and
$Q_i$=flowrate at $x_i$.
$R_{loss}$ may be determined by various methods. For example, $R_{loss}$ may be chosen as a predetermined value (e.g., zero), determined using any empirical model, or learned using machine learning.

Exemplary errors in this reduced order model (compared with fully 3D CFD calculations) may fall into two main categories: (1) invalid assumptions in reduced order resistance models and (2) geometric errors induced by the geometry simplification process. The main contribution to the first type of error may lie in the assumption of laminar flow underlying the accuracy of both resistance models. Though the assumption may operate in healthy arterial regions away from branching locations, highly non-laminar flows may exist at both branching locations and in the expansion region after a stenosed region. The second category of ROM errors may be dependent on the method used in created the simplified geometry, e.g., creating the centerline points and defining the radii at each point.

Overall, the system may be represented as $$P_{i+1} - P_i(R_{i,ML}(Q))Q_i$$

where $R_{i,ML}(Q) = R_{poisseuille} + R_{bernoulli} + \Delta R_i(Q)$, and the loss, $\Delta R_i(Q)$, may be calculated from data, which may depend on the flow-rate. In some embodiments, the differences in resistance may be approximated using a machine learning approximation, e.g., $$\Delta R_{i,ML}(Q) \sim \Delta R_i(Q) = R_{CFD} - R_{poisseuille} - R_{bernoulli}$$

At step 316, the determined one or more impedance values for blood flow through the region(s) may be integrated and/or built into a reduced order model.

The integrated reduced order model may be used to estimate and/or determine blood flow characteristics (e.g., as in method 400C of FIG. 4C), described herein. The integrated reduced order model may also be used for planning treatments of lesions, e.g., by altering an impedance value or a geometric feature (simplified from a 3D image data), and/or simulate blood flow. In some embodiments, the integrated reduced order model may be output to an electronic storage medium and/or display of server systems 106.

Figure 4A:
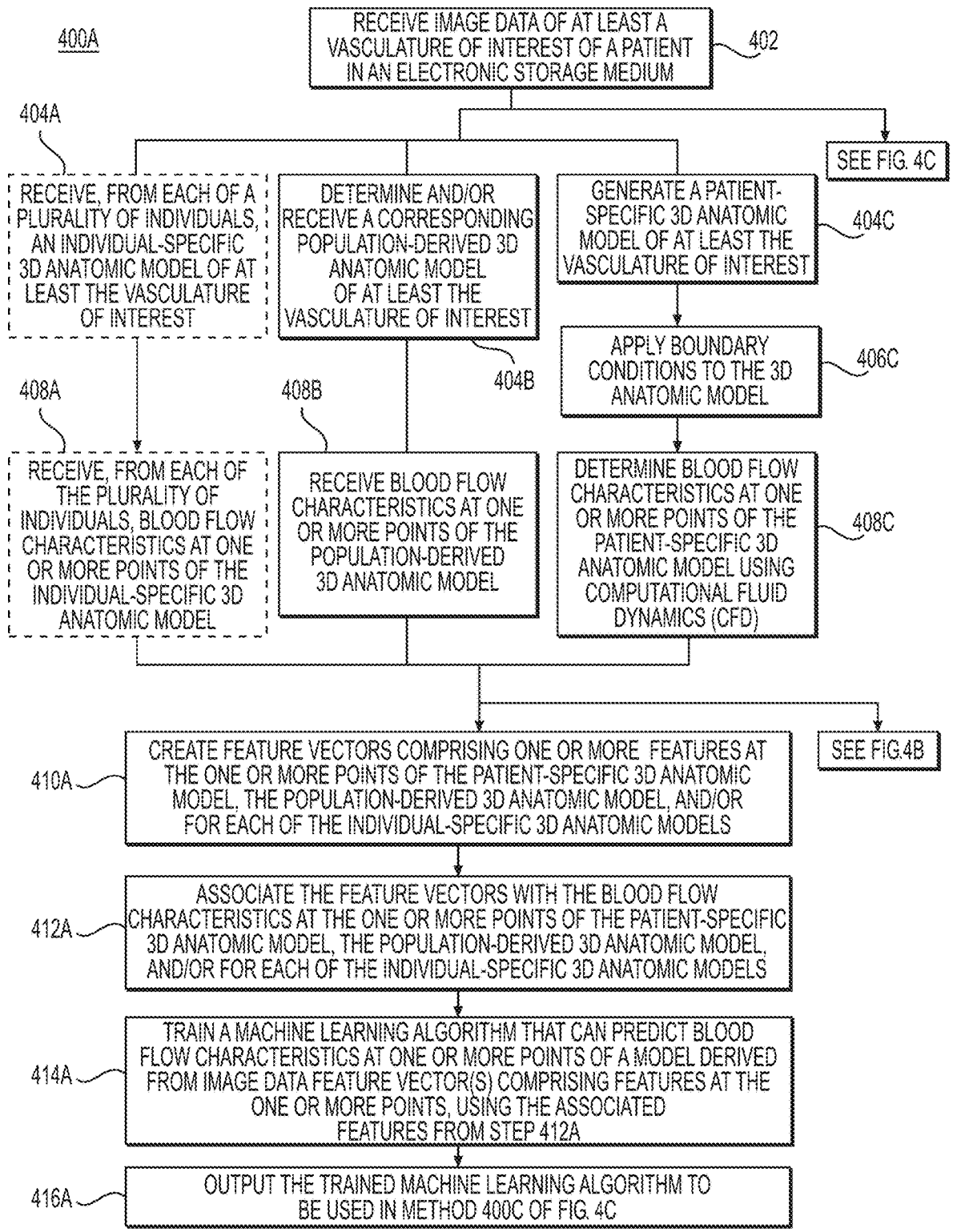
FIGS. 4A-4C are block diagrams of exemplary methods 400A-400C of training and executing a machine learning algorithm to estimate blood flow characteristics using a reduced order model, according to an exemplary embodiment of the present disclosure.
Figure 4B:
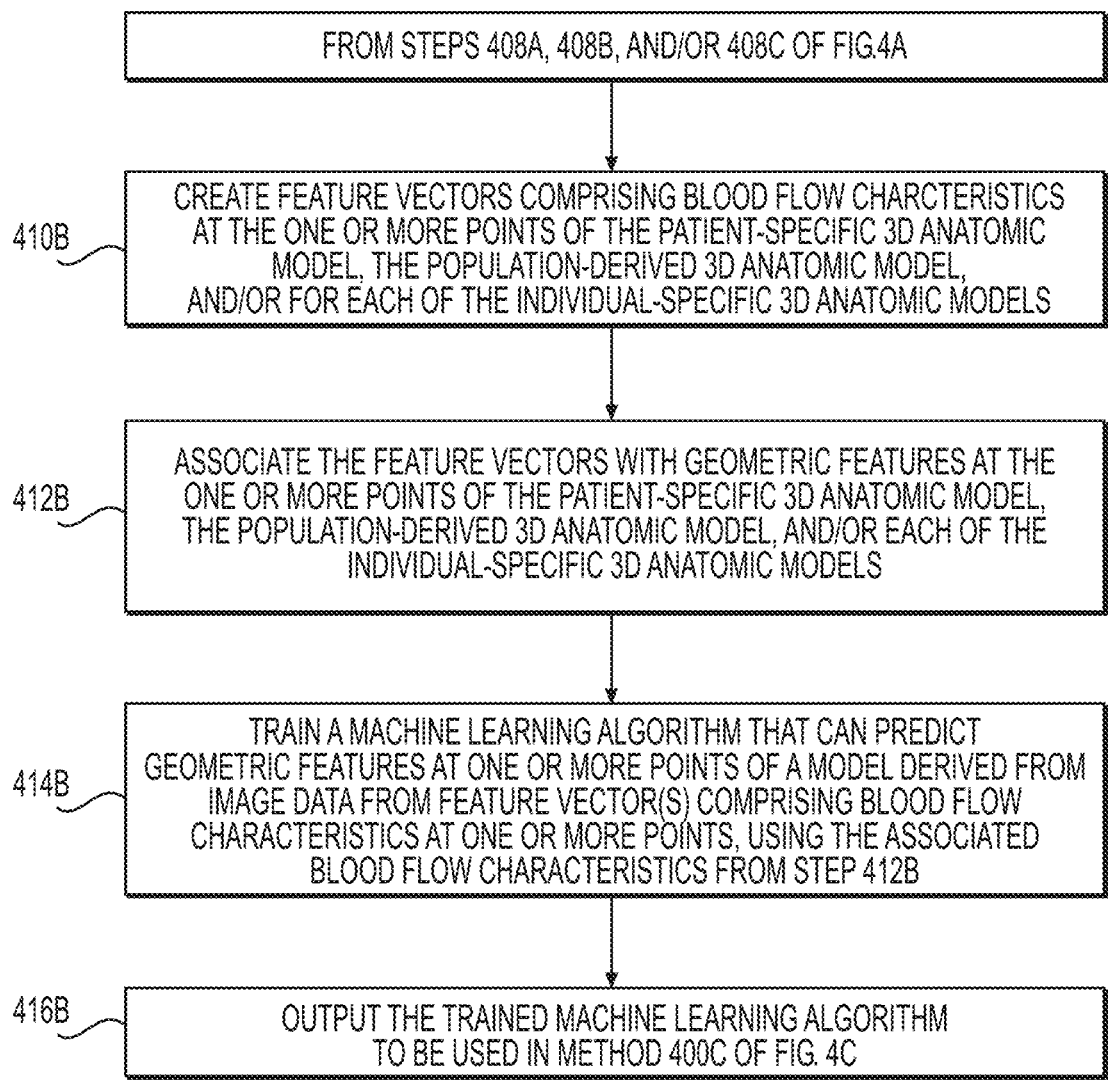
Figure 4C:
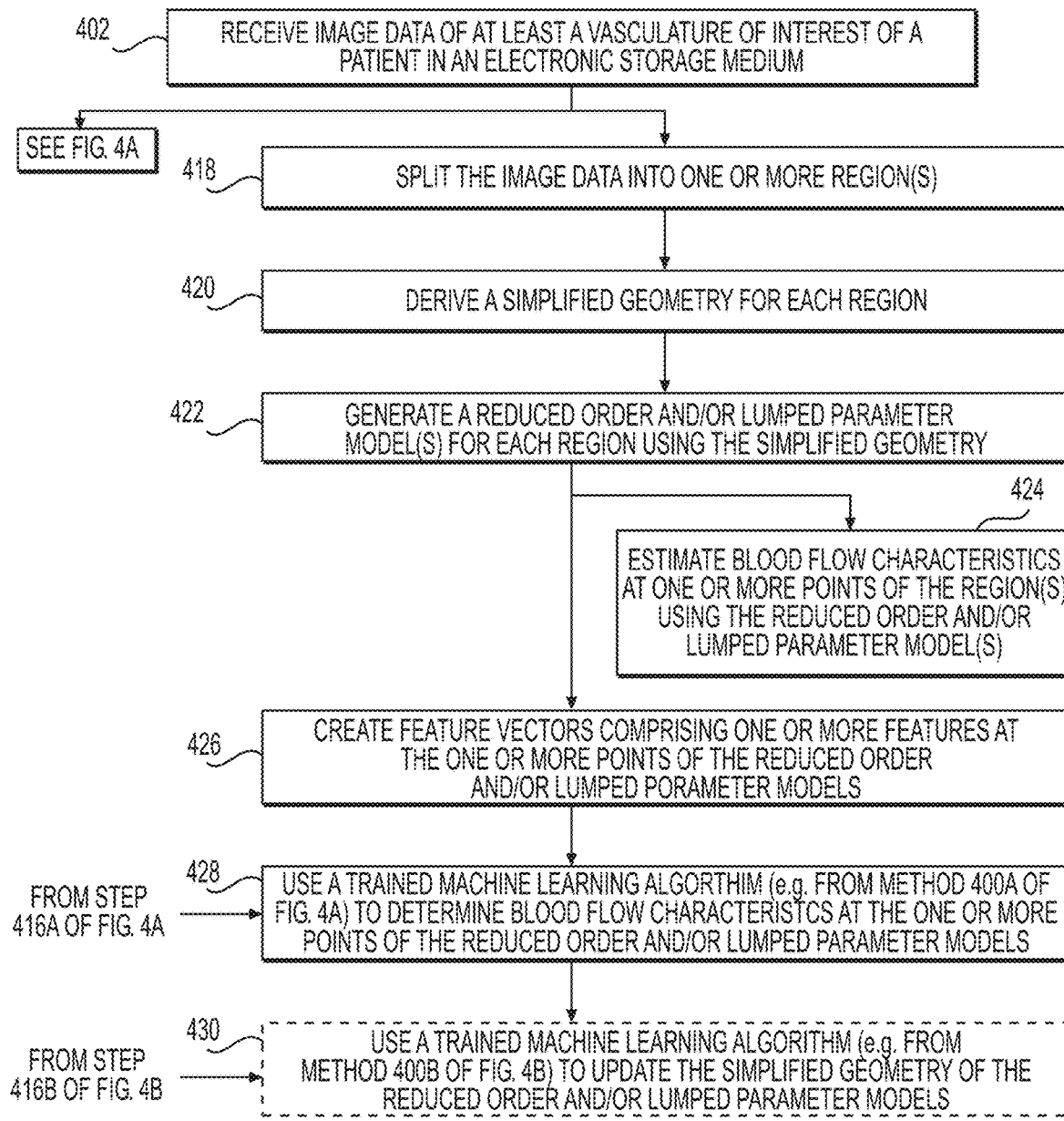

FIGS. 4A-4C are block diagrams of exemplary methods 400A-400C of training and applying a machine learning algorithm for an estimation of blood flow characteristics using a reduced order model, according to an exemplary embodiment of the present disclosure. Moreover, FIG. 4A depicts an exemplary method 400A of training a machine learning algorithm to predict blood flow characteristics of a model derived from image data (e.g., a reduced order or lumped parameter model). FIG. 4B depicts an exemplary method 400B of training a machine learning algorithm to predict geometric features of a model derived from image data (e.g., simplified geometric features of a reduced order or lumped parameter model) using blood flow characteristics. FIG. 4C depicts an exemplary method 400C of applying a trained machine learning algorithm to determine blood flow characteristics (e.g., more accurately) using a reduced order or lumped parameter model, or to determine geometric features of a model.

Referring now to FIG. 4A, which discloses an exemplary method of training a machine learning algorithm to predict blood flow characteristics, step 402 may include receiving image data of at least a vasculature of interest of a patient in an electronic storage medium. The received image data may be used, for example, to generate a patient-specific 3D anatomic model of at least the vasculature of interest (e.g., as in 404C). Step 406C may include applying boundary conditions to the generated 3D anatomic model. Further, step 408C may include determining blood flow characteristics at one or more points of the patient-specific 3D anatomic model using computational fluid dynamics (CFD) (e.g., using Navier-Stokes equations). In some embodiments, steps 406C and 408C may use methods described in steps 206, 210B and 212B of method 200, as depicted in FIG. 2).

The received image data may also be used to determine and/or receive a corresponding population-derived 3D anatomic model of at least the vasculature of interest (e.g., as in step 404B). In such embodiments, step 408B may include receiving blood flow characteristics at one or more points of the population-derived 3D anatomic model.

In some embodiments, independently or with the use of the received image data, step 404A may include receiving, from each of a plurality of individuals, an individual-specific 3D anatomic model of at least the vasculature of interest. In such embodiments, step 408A may include receiving, from each of the plurality of individuals, blood flow characteristics at one or more points of the individual-specific 3D anatomic model.

It is contemplated that in some embodiments, physiological and/or phenotypic parameters as it relates to the anatomic model may also be received, e.g., from the patient in step 404C, from population derived data from 404B, or from each of the plurality of individuals in 404A. These physiological and/or phenotypic parameters may be included in the features used to form the feature vector in step 410A described herein.

For steps 404A and 404B, the type of anatomic models selected or individuals from which the model is received may be guided by the original received image data or patient (e.g., from step 402). Thus, steps 404A-404C are examples of steps to receive a 3D anatomical model to develop feature vectors as part of the domain for a training data set for a machine-learning algorithm. Steps 408A-408C may be examples of steps to receive blood flow characteristics for one or more points of the 3D anatomic models from steps 404A-404C, and the blood flow characteristics determined in steps 408A-408C may serve as the range for the training data set of the machine-learning algorithm.

Step 410A may include creating feature vectors comprising of one or more features at the one or more points of the patient-specific 3D anatomic model (e.g., subsequent to steps 404C, 406C, and/or 408C). In some embodiments, the feature vectors may be formed for one or more points of the population derived 3D anatomic model (e.g., subsequent to steps 404B and/or 408B). Alternatively or additionally, the feature vectors may be formed for one or more points of each or some of the individual-specific 3D anatomic models (e.g., subsequent to steps 404A and/or 408A). The feature vectors may be formed for points in the 3D anatomic models for which there is a received or determined blood flow characteristic. The features of the feature vector may include a numerical description of the patient-specific geometry at that point and estimates of physiological or phenotypic parameters of the patient or individual of which the anatomic model is received. The physiological and/or phenotypic parameters may include, but are not limited to, for example, (i) biographical characteristics: patient age, gender, height, weight, etc.; (ii) disease characteristics: presence or absence of diabetes, myocardial infarction, malignant and rheumatic conditions, peripheral vascular conditions, etc.; (iii) lifestyle characteristics: presence or absence of current medications/drugs, smoker/non-smoker; (iv) hemodynamic forces: axial plaque stress, wall shear stress, etc., (v) systolic and diastolic blood pressures; and (vi) blood properties including: plasma, red blood cells (erythrocytes), hematocrit, white blood cells (leukocytes) and platelets (thrombocytes), viscosity, yield stress. The feature vector may contain both global and local physiological or phenotypic parameters, where: for global parameters, all points have the same numerical value; and for local parameters, the value(s) may change at different points in the feature vector. Server systems 106 may then associate this feature vector with the received or simulated value of the blood flow characteristic at this point. Thus, step 412A may include associating the feature vectors with the blood flow characteristics at the one or more points of the patient-specific 3D anatomic model, the population-derived 3D anatomic model, and/or of each of the individual-specific 3D anatomic models.

Step 414A may include training a machine-learning algorithm to predict blood flow characteristics at one or more points of a model derived from image data from feature vector(s) at the one or more points. The training may use the associated features from step 412A, for example, to determine relations and/or feature weights. Examples of machine learning algorithms that can perform this task are support vector machines (SVMs), neural networks, multi-layer perceptrons (MLPs), multivariate regression (MVR) (e.g., weighted linear or logistic regression), and/or other supervised machine learning techniques known to persons having ordinary skill in the art. Server systems 106 may then save the results of the machine-learning algorithm (e.g., feature weights) to a digital representation (e.g., the memory or digital storage (e.g., hard drive, network drive) of a computational device such as a computer, laptop, DSP, server, etc.). The stored feature weights may define the extent to which features (e.g., geometrical description, boundary conditions, physiological and/or phenotypic parameters, anatomical characteristics, etc.) are predictive of the blood flow and/or blood pressure at one or more points of the model or the system represented by the model.

Step 416A may include outputting the trained machine learning algorithm (e.g., to an electronic storage medium). The trained machine learning algorithm may be used in method 400C of FIG. 4C, e.g., to determine blood flow characteristics from a model having a simplified geometry (e.g., a reduced order or lumped parameter model).

FIG. 4B depicts an exemplary method 400B of training a machine learning algorithm to predict geometric features at one or more points of a model derived from image data, e.g., from feature vectors comprising blood flow characteristics at the one or more points. Steps 402, 408A-C, 406, and/or 408A-C of method 400A depicted in FIG. 4A may be performed prior to steps of method 400B depicted in FIG. 4B.

Step 410B may include creating feature vectors comprising blood flow characteristics at the one or more points of the patient-specific 3D anatomic model. (e.g., subsequent to steps 404C, 406C, and/or 408C). In some embodiments, the feature vectors may be formed for one or more points of the population derived 3D anatomic model (e.g., subsequent to steps 404B and/or 408B). Alternatively or additionally, the feature vectors may be formed for one or more points of each or some of the individual-specific 3D anatomic models (e.g., subsequent to steps 404A and/or 408A). The feature vectors may be formed for points in the 3D anatomic models for which there are known geometric features. These geometric features may include a numerical description of the patient-specific geometry at that point. The feature vector may contain both global and local physiological or phenotypic parameters, where: for global parameters, all points have the same numerical value; and for local parameters, the value(s) may change at different points in the feature vector. Server systems 106 may then associate this feature vector with the received or simulated value of the blood flow characteristic at this point. Thus, step 412B may include associating the feature vectors comprising blood flow characteristics at one or more points of the patient-specific 3D anatomic model, and/or of each of the individual-specific 3D anatomic models with the geometric features at the one or more points.

Step 414B may include training a machine-learning algorithm to predict geometric features at one or more points of a model derived from image data from feature vector(s) comprising blood flow characteristics at the one or more points. The training may use the associated features from step 412B, for example, to determine relations and/or feature weights. Examples of machine learning algorithms that can perform this task are support vector machines (SVMs), neural networks, multi-layer perceptrons (MLPs), multivariate regression (MVR) (e.g., weighted linear or logistic regression), and/or other supervised machine learning techniques known to persons having ordinary skill in the art. Server systems 106 may then save the results of the machine-learning algorithm (e.g., feature weights) to a digital representation (e.g., the memory or digital storage [e.g., hard drive, network drive] of a computational device such as a computer, laptop, DSP, server, etc.). The stored feature weights may define the extent to which the blood flow characteristics are predictive of geometric features at one or more points of the model or the system represented by the model.

Step 416B may include outputting the trained machine learning algorithm (e.g., to an electronic storage medium). The trained machine learning algorithm may be used in method 400C of FIG. 4C, e.g., to update, further refine, and/or generate geometric features of a model derived from image data. This model may be a 2D or 3D anatomical model or may have a simplified geometry (e.g., a reduced order or lumped parameter model).

FIG. 4C depicts an exemplary method 400C of applying a trained machine learning algorithm to determine blood flow characteristics (e.g., more accurately) using a reduced order or lumped parameter model, or to determine geometric features of a model.

Step 402 may include receiving image data of at least a vasculature of interest of the patient in an electronic storage medium (e.g., as in methods 400A and 400B). The image data may be received from one or more image scanning modality (e.g., computed tomography, angiography, magnetic resonance, X ray, etc.), an electronic storage medium, a third party device, or via cloud.

Having completed the steps for training a machine learning algorithm in methods 400A and/or 400B, or having received a trained machine learning algorithm as described in these methods, step 418 through 430 describe the application of these trained machine learning algorithms towards, e.g., determining blood flow characteristics and/or geometric features.

For example, step 418 may include splitting the image data (received in step 402) into one or more region(s). Step 418 may be similar to steps 204 or 210A of method 200 depicted in FIG. 2 or step 308 of FIG. 3. In some embodiments, the splitting may be based on estimated blood flow characteristics or may occur manually or automatically to identify voxels belonging to the various regions (e.g., aorta to the lumen of the coronary arteries).

Step 420 may include deriving a simplified geometry for each region. Step 420 may be similar to step 312 of method 300, as depicted in FIG. 3.

Step 422 may include generating reduced order and/or lumped parameter model(s) for each (or one or more) region(s) using the simplified geometry. Method 300 in FIG. 3 describes, broadly at least some embodiments for this generation step.

Step 426 may include creating feature vectors comprising one or more features at the one or more points of the reduced order and/or lumped parameter models. The features may reflect or be similar to the features used in the training phase described in method 400A. In some embodiments, these features may include, but are not limited to, a local radius or diameter, a local indicia of a severity of a stenosis (e.g., percentage), a minimum upstream diameter, a minimum upstream indicia of the severity of a stenosis, a minimum downstream diameter, a minimum downstream indicia of the severity of a stenosis, a distance to the nearest bifurcation, a diameter of the nearest upstream bifurcation, a distance to an ostium, an average downstream outlet diameter, a minimum downstream outlet diameter, a minimum, maximum, mean, or median downstream resistances (e.g., or boundary conditions), aortic pressure, and physiological and/or phenotypic parameters described above.

In some embodiments, the feature vectors may include, e.g., as features, blood flow characteristics at one or more points that have been estimated using the reduced order and/or lumped parameter model(s). In such embodiments, step 424 may include estimating the blood flow characteristics at one or more points of the region(s) using the reduced order and/or lumped parameter model(s).

Step 428 may include using a trained machine learning algorithm (e.g., from method 400A of FIG. 4A) to determine blood flow characteristics at the one or more points of the reduced order and/or lumped parameter models. The blood flow characteristics may be determined for one or more points of each region, individually, or may be solved for the whole vasculature or system. In some embodiments, the blood flow characteristics may be displayed, for example, on an anatomic model, or may be used as part of a simulation of blood flow. In further embodiments, the blood flow characteristics may be used to determine important indicia of perfusion and/or tissue viability (e.g., a myocardial perfusion risk index). Likewise, if a vasculature has one or more lesions or stenotic regions, the blood flow characteristics may be used to determine an indicia of severity for the lesions or stenotic regions (e.g., a plaque vulnerability index).

Additionally or alternately, as shown in step 430, a trained machine learning algorithm (e.g., from method 400B of FIG. 4B) may be used to update the simplified geometry of the reduced order and/or lumped parameter models. In some embodiments, step 430 may be used to determine geometric features for generating a non-simplified model (e.g., a 2D or 3D anatomic model). In some embodiments, the updated model(s), or determined geometric features may be output to an electronic storage medium or display.

In forming the feature vector, e.g., in methods 400A of FIG. 4A and method 400C of FIG. 4B, the feature vector may include, but are not limited to: (vii) characteristics of the vessel geometry (Cross-sectional area of the aortic inlet and outlet, surface area and volume of the aorta, Minimum, maximum, and average cross-sectional area, etc.); (viii) characteristics of the coronary branch geometry; and (ix) one or more feature sets.

In one embodiment, the characteristics of the coronary branch geometry may include: (i) volumes of the aorta upstream/downstream of the coronary branch point; (ii) cross-sectional area of the coronary/aorta bifurcation point, i.e., inlet to the coronary branch; (iii) total number of vessel bifurcations, and the number of upstream/downstream vessel bifurcations; (iv) average, minimum, and maximum upstream/downstream cross-sectional areas; (v) distances (along the vessel centerline) to the centerline point of minimum and maximum upstream/downstream cross-sectional areas; (vi) cross-sectional of and distance (along the vessel centerline) to the nearest upstream/downstream vessel bifurcation; (vii) cross-sectional area of and distance (along the vessel centerline) to the nearest coronary outlet and aortic inlet/outlet; (viii) cross-sectional areas and distances (along the vessel centerline) to the downstream coronary outlets with the smallest/largest cross-sectional areas; (ix) upstream/downstream volumes of the coronary vessels; and (x) upstream/downstream volume fractions of the coronary vessel with a cross-sectional area below a user-specified tolerance.

In one embodiment, a first feature set may define cross-sectional area features, such as a cross-sectional lumen area along the coronary centerline, a powered cross-sectional lumen area, a ratio of lumen cross-sectional area with respect to the main ostia (LM, RCA), a powered ratio of lumen cross-sectional area with respect to the main ostia, a degree of tapering in cross-sectional lumen area along the centerline, locations of stenotic lesions, lengths of stenotic lesions, location and number of lesions corresponding to 50%, 75%, 90% area reduction, distance from stenotic lesion to the main ostia, and/or irregularity (or circularity) of cross-sectional lumen boundary.

In one embodiment, the cross-sectional lumen area along the coronary centerline may be calculated by extracting a centerline from constructed geometry, smoothing the centerline if necessary, and computing cross-sectional area at each centerline point and map it to corresponding surface and volume mesh points. In one embodiment, the powered cross-sectional lumen area can be determined from various source of scaling laws. In one embodiment, the ratio of lumen cross-sectional area with respect to the main ostia (LM, RCA) can be calculated by measuring cross-sectional area at the LM ostium, normalizing cross-sectional area of the left coronary by LM ostium area, measuring cross-sectional area at the RCA ostium, and normalizing cross-sectional area of the right coronary by RCA ostium area. In one embodiment, the powered ratio of lumen cross-sectional area with respect to the main ostia can be determined from various source of scaling laws. In one embodiment, the degree of tapering in cross-sectional lumen area along the centerline can be calculated by sampling centerline points within a certain interval (e.g., twice the diameter of the vessel) and compute a slope of linearly-fitted cross-sectional area. In one embodiment, the location of stenotic lesions can be calculated by detecting minima of cross-sectional area curve, detecting locations where first derivative of area curve is zero and second derivative is positive, and computing distance (parametric arc length of centerline) from the main ostium. In one embodiment, the lengths of stenotic lesions can be calculated by computing the proximal and distal locations from the stenotic lesion, where cross-sectional area is recovered.

In one embodiment, another feature set may include intensity features that define, for example, intensity change along the centerline (slope of linearly-fitted intensity variation). In one embodiment, another feature set may include surface features that define, for example, 3D surface curvature of geometry (Gaussian, maximum, minimum, mean). In one embodiment, another feature set may include volume features that define, for example, a ratio of total coronary volume compared to myocardial volume. In one embodiment, another feature set may include centerline features that define, for example, curvature (bending) of coronary centerline, e.g., by computing Frenet curvature:

$$\kappa = \frac{|p' \times p''|}{|p'|^3},$$

where p is coordinate of centerline or by computing an inverse of the radius of circumscribed circle along the centerline points. Curvature (bending) of coronary centerline may also be calculated based on tortuosity (non-planarity) of coronary centerline, e.g., by computing Frenet torsion:

$$\tau = \frac{(p' \times p'') \cdot p'''}{|p' \times p''|^2},$$

where p is coordinate of centerline

In one embodiment, another feature set may include a SYNTAX scoring feature, including, for example, an existence of aorto ostial lesion, detection of a lesion located at the origin of the coronary from the aorta; and/or dominance (left or right).

In one embodiment, another feature set may include a simplified physics feature, e.g., including a fractional flow reserve value derived from Hagen-Poisseille flow assumption (Resistance~Area$^{-2}$). For example, in one embodiment, server systems 106 may compute the cross-sectional area of the origin (LM ostium or RCA ostium) of the coronary from the aorta ($A_0$) with aortic pressure ($P_0$); compute cross-sectional area of coronary vessel ($A_i$) at each sampled interval ($L_i$); determine the amount of coronary flow in each segment of vessel using resistance boundary condition under hyperemic assumption ($Q_i$); estimate resistance at each sampled location ($R_i$) based on:

$$R_i = \alpha_i \frac{8\mu L_i}{\pi A_i^{\gamma_i}} + \beta_i,$$

where:

Nominal value μ=dynamic viscosiy of blood, $\alpha_i$=1.0, $\beta_i$=0, $\gamma_i$=2.0 (Hagen—Poisseille).

Server systems 106 may estimate pressure drop ($\Delta P_i$) as $\Delta P_i = Q_i R_i$ and compute FFR at each sampled location as $$FFR_i = \frac{P_0 - \sum_{k=1}^{i} \Delta P_k}{P_0}.$$

Locations of cross-sectional area minima or intervals smaller than vessel radius may be used for sampling locations. Server systems 106 may interpolate FFR along the centerline using $FFR_i$, project FFR values to 3D surface mesh node, and vary $\alpha_i$, $\beta_i$, $\gamma_i$ and obtain new sets of FFR estimation as necessary for training, such as by using the feature sets defined above to perturb parameters where $\alpha_i$, $\beta_i$ can be a function of the diseased length, degree of stenosis and tapering ratio to account for tapered vessel; and $Q_i$ can be determined by summing distributed flow of each outlet on the basis of the same scaling law as the resistance boundary condition (outlet resistance∝outlet area$^{-1.35}$). However, a new scaling law and hyperemic assumption can be adopted, and this feature vector may be associated with the measurement or simulated value of the FFR at that point.

It is contemplated that in some embodiments a trained machine learning algorithm that predicts blood flow characteristics or geometric features from feature vectors may merely be received, e.g., in an electronic storage medium, and readily implemented in method 400C of FIG. 4C. In such embodiments, the training of such a machine-learning algorithm by server systems 106 may be rendered unnecessary.

It is further contemplated that in various embodiments, other models may be used other than a 3D anatomical model in either of the steps presented herein. For example, a 2D model may be used and/or a temporal component may be added to the models.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of determining blood flow characteristics of a patient, the method comprising:
    obtaining a reduced-order model that is representative of at least a portion of a patient-specific anatomic model of at least a portion of a patient's vasculature, the reduced-order model including one or more points having an impedance value based on first estimated values of blood flow characteristics at a first set of one or more locations of the portion of the patient-specific anatomic model;
    updating the reduced-order model by employing a machine-learning algorithm that has been trained, based on errors determined between at least one impedance value of at least one training reduced-order model and at least one corresponding impedance value determined by computational fluid dynamics, to reduce error in one or more impedance values of an input reduced-order model; and
    using the updated reduced-order model to determine second estimated values for the blood flow characteristic at a second set of one or more locations of the portion of the patient-specific anatomic model, the second set being different from the first set.

2. The computer-implemented method of claim 1, wherein:
    a plurality of reduced order models are obtained, each model representative of a different portion of the patient-specific anatomic model;
    each model is updated using the machine-learning algorithm; and
    the plurality of models are used in combination to determine the second estimated values.

3. The computer-implemented method of claim 2, wherein the plurality of reduced order models are obtained by:
    splitting the portion of the patient-specific anatomic model into a plurality of regions of the patient's vasculature; and
    generating a respective reduced order model for each region.

4. The computer-implemented method of claim 3, wherein the splitting is based on the first estimated values of the blood flow characteristics.

5. The computer-implemented method of claim 3, wherein the splitting is configured to distinguish between one or more healthy regions of the patient's vasculature and one or more unhealthy regions of the patient's vasculature.

6. The computer-implemented method of claim 5, wherein the one or more unhealthy regions of the patient's vasculature include one or more of an ostial bifurcation, a non-ostial bifurcation, a stenosed region, or an expansion region.

7. The computer-implemented method of claim 1, wherein the blood flow characteristics include one or more of: a blood pressure, a fractional flow reserve (FFR), a blood flow rate or a flow velocity, a velocity or pressure field, a hemodynamic force, and an organ and/or tissue perfusion characteristic.

8. The computer-implemented method of claim 1, further comprising:
    representing a treatment or intervention as a modification to or value of a reduced order model; and
    modifying the reduced order model to include the modification or value, such that the second estimated values are indicative of a condition of the patient after application of the treatment or intervention.

9. The computer-implemented method of claim 8, further comprising:

generating a modified patient-specific anatomic model based on one or more of the modified reduced order model or the second estimated values determined using the modified reduced order model.

10. A system for determining blood flow characteristics of a patient, the system comprising:

at least one memory storing instructions and a machine-learning algorithm trained, based on errors determined between at least one impedance value of at least one training reduced-order model and at least one corresponding impedance value determined by computational fluid dynamics, to reduce error in one or more impedance values of an input reduced-order model; and at least one processor operatively connected to the memory and configured to execute the instructions to perform operations, including:

obtaining a reduced-order model that is representative of at least a portion of a patient-specific anatomic model of at least a portion of a patient's vasculature, the reduced-order model including one or more points having an impedance value based on first estimated values of blood flow characteristics at a first set of one or more locations of the portion of the patient-specific anatomic model;

updating the reduced-order model by employing the machine-learning algorithm; and using the updated reduced-order model to determine second estimated values for the blood flow characteristic at a second set of one or more locations of the portion of the patient-specific anatomic model, the second set being different from the first set.

11. The system of claim 10, wherein:

a plurality of reduced order models are obtained, each model representative of a different portion of the patient-specific anatomic model;

each model is updated using the machine-learning algorithm; and the plurality of models are used in combination to determine the second estimated values.

12. The system of claim 11, wherein the plurality of reduced order models are obtained by:

splitting the portion of the patient-specific anatomic model into a plurality of regions of the patient's vasculature; and generating a respective reduced order model for each region.

13. The system of claim 12, wherein:

the splitting is based on the first estimated values of the blood flow characteristics; and the splitting is configured to distinguish between one or more healthy regions of the patient's vasculature and one or more unhealthy regions of the patient's vasculature including one or more of an ostial bifurcation, a non-ostial bifurcation, a stenosed region, or an expansion region.

14. The system of claim 10, wherein the blood flow characteristics include one or more of: a blood pressure, a fractional flow reserve (FFR), a blood flow rate or a flow velocity, a velocity or pressure field, a hemodynamic force, and an organ and/or tissue perfusion characteristic.

15. The system of claim 10, wherein the operations further include:

representing a treatment or intervention as a modification to or value of a reduced order model; and modifying the reduced order model to include the modification or value, such that the second estimated values are indicative of a condition of the patient after application of the treatment or intervention.

16. The system of claim 15, wherein the operations further include:

generating a modified patient-specific anatomic model based on one or more of the modified reduced order model or the second estimated values determined using the modified reduced order model.

17. A non-transitory computer-readable medium comprising instructions for determining blood flow characteristics of a patient that are executable by at least one processor to perform operations, the operations including:

obtaining a reduced-order model that is representative of at least a portion of a patient-specific anatomic model of at least a portion of a patient's vasculature, the reduced-order model including one or more points having an impedance value based on first estimated values of blood flow characteristics at a first set of one or more locations of the portion of the patient-specific anatomic model;

updating the reduced-order model by employing a machine-learning algorithm that has been trained, based on errors determined between at least one impedance value of at least one training reduced-order model and at least one corresponding impedance value determined by computational fluid dynamics, to reduce error in one or more impedance values of an input reduced-order model; and using the updated reduced-order model to determine second estimated values for the blood flow characteristic at a second set of one or more locations of the portion of the patient-specific anatomic model, the second set being different from the first set.

18. The non-transitory computer-readable medium of claim 17, wherein:

a plurality of reduced order models are obtained, each model representative of a different portion of the patient-specific anatomic model;

each model is updated using the machine-learning algorithm; and the plurality of models are used in combination to determine the second estimated values.

19. The non-transitory computer-readable medium of claim 18, wherein the plurality of reduced order models are obtained by:

splitting the portion of the patient-specific anatomic model into a plurality of regions of the patient's vasculature; and generating a respective reduced order model for each region.

20. The non-transitory computer-readable medium of claim 19, wherein:

the splitting is based on the first estimated values of the blood flow characteristics; and the splitting is configured to distinguish between one or more healthy regions of the patient's vasculature and one or more unhealthy regions of the patient's vasculature including one or more of an ostial bifurcation, a non-ostial bifurcation, a stenosed region, or an expansion region.

* * * * *